United States Patent [19]

Rappaport

[11] 4,174,702
[45] * Nov. 20, 1979

[54] DISPOSABLE CATALYTIC HEATER

[76] Inventor: Alfred A. Rappaport, Apt. 305 2081 S. Ocean Dr., Hallandale, Fla. 33009

[ * ] Notice: The portion of the term of this patent subsequent to Jan. 17, 1995, has been disclaimed.

[21] Appl. No.: 842,050

[22] Filed: Oct. 14, 1977

[51] Int. Cl.² .............................................. A61F 7/06
[52] U.S. Cl. ................................................... 126/208
[58] Field of Search ...................... 126/208; 23/288 F; 21/117; 422/1

[56] References Cited

U.S. PATENT DOCUMENTS

| | | | |
|---|---|---|---|
| 1,502,251 | 7/1924 | Kanazawa | 126/208 |
| 2,670,728 | 3/1954 | Smith | 126/208 |
| 2,746,138 | 5/1956 | Smith | 126/208 |
| 2,914,060 | 11/1959 | Wilcox | 126/208 |
| 2,942,601 | 6/1960 | Smith | 126/208 |
| 3,046,975 | 7/1962 | Gottwald | 126/208 |
| 3,049,117 | 8/1962 | Matoba | 126/208 |
| 3,119,650 | 1/1964 | Bilyeu | 126/208 |
| 3,295,510 | 1/1967 | Matoba | 126/208 |
| 3,362,783 | 1/1968 | Leak | 23/288 F |
| 3,405,704 | 10/1968 | Wintz | 126/208 |
| 3,420,221 | 1/1969 | Wintz | 126/208 |
| 4,068,651 | 1/1978 | Rappaport | 126/208 |

Primary Examiner—Carroll B. Dority, Jr.
Assistant Examiner—Lee E. Barrett
Attorney, Agent, or Firm—Gustave Miller

[57] ABSTRACT

This is a catalytic heater which is so inexpensive that it may be used as a disposable heater. It has a lower container section or fuel cartridge and wick for the fuel and any other liquid that may be present for dispensing. It is used together with an upper chimney container section. Alternately, only the fuel cartridge may be disposed of, and a new fuel cartridge may be mated with the previously used upper chimney section. A catalytic impregnated stainless steel member is reuseable along with a snuffer to be secured to the upper chimney section. The catalytic impregnated member is stainless steel, of approximately 0.0037 gauge, and may be either a foraminated plate or a wire mesh screen woven approximately 80 strands to the inch. A filter made of activated charcoal or any other comparable filtering material may also be provided over the fuel supply.

In addition, the fuel compartment may be divided by vertical partitions into two or three compartments, particularly for use with liquids, such as insect repellants and other chemicals that are not miscible with liquid fuel.

A fuel material with an upstanding wick is provided in the lower container section, and a snuffer tube is located in the upper chimney section for snuffing out the flame on the wick and thus permitting the catalytic heating action to continue. An insulating coating is provided on both sections to retain the heat, and to make it possible to carry the heater without it being too hot for comfort.

20 Claims, 12 Drawing Figures

DISPOSABLE CATALYTIC HEATER

BACKGROUND OF THE INVENTION

Small, pocket size hand warmers and scent propagators are well known, as illustrated in U.S. Pat. Nos. 1,502,251; 2,670,728; 2,746,138; 2,821,570; 2,914,060; 2,942,601; 3,049,117; 3,046,975; 3,049,117; 3,119,650, 3,295,510, 3,405,704; and 3,420,221. These all have one feature in common, the fuel must be poured in the absorbent material by the user, with its attending dangers. Too much fuel, there is danger of a fire, and, also, the excess fuel may make the catalytic material inoperative. The two patents to Smith and Gottwald show the methods of making the catalytic member. There is no provision in any of these patents that they can be used as other than a hand or human body warmer, except in U.S. Pat. No. 3,119,650, which also discloses using the heat to propagate a scent for attracting wild game.

SUMMARY OF THIS INVENTION

This invention is an inexpensive disposable catalytic heater which may be made up solely for use as a hand and body heater, and also may be made up for dispensing scents or chemicals for repelling insects and other pests, or for heating or cooking purposes. If the scent or chemical is miscible with the fuel, only a single compartment is provided in the cartridge; if non-miscible, the fuel and the scent or chemicals are located in different compartments.

This invention consists of inexpensive metal fuel cartridge and chimney sections, alluminum for instance, that is coated with a heat insulating material to retain the heat and to make it possible to carry the heater without it being too hot for comfort. The two sections are mated together, and they have between them a catalyst impregnated stainless steel foraminated single plane plate or mesh mounted in a frame that is held between the sections, the catalyst member having an opening through which is extended a wick from a fuel or a fuel absorbent material in the cartridge section.

When desired, the fuel may be mixed with a miscible scent or insect repellant. If non-miscible, the cartridge is provided with a separate compartment for each liquid. The catalyst member is impregnated with platinum or palladium, as set forth in the two Smith U.S. Pat. Nos. 2,670,728 and 2,746,138, and also the Gottwald U.S. Pat. No. 2,821,510. A removable cover is provided on the lower or cartridge section, and the cover may be hermetically sealed for peeling off, or may be a paint can type cover or a snap-on sealing cover.

The chimney or upper section has a snuffer tube located to come down about the opening through which the wick extends, to snuff the flame. When all the fuel and liquids are in the fuel cartridge, the snuffer tube is attached to the inside of the roof of the chimney section. When only fuel is provided in the cartridge section, an insertable container is provided in the chimney, which may have either liquid chemicals, food or beverages, as desired. A removable cover on this insertable container is provided to be removed when the container is inserted through the roof of the chimney section. A tubular snuffer is integrally provided on the center of the bottom of the insertable container of a size to just come down about the wick opening or eyelet when the container is inserted through the chimney section.

OBJECTS OF THE INVENTION

It is an object of this invention to provide an inexpensive, catalytic heater, particularly for use by the hands and for the body, that may be partially or completely disposed of when through using.

A further object of this invention is to provide a pocket carried hand and/or body heater that may be solely a heater, and also may be set up as an insect repellant.

Yet a further object of this invention is to provide an inexpensive heater that may have either a single solid fuel or liquid fuel and mixed chemical compartment, or alternately may have two or three separate compartments for use with non-miscible liquids.

Still a further object of this invention is to provide a catalytic heater having a disposable fuel containing lower section that has a cover sealed thereon until it is ready to be used, by removing the cover, lighting the wick, then mating it with the upper chimney section to snuff out the wick flame and thus continue the catalytic process of producing the heating action.

Still yet a further object of this invention is to provide a heat insulating coating on the heater to retain the heat at its highest possible temperature and also enable the heater to be used and carried comfortably on one's person.

Yet a further object of this invention is to provide a new type of an inexpensive catalyst that can be made to fit any size or type of catalytic heater.

A still further object of this invention is to provide a catalyst that has a flat surface completely exposed to the fumes of the fuel, thus providing prompt ignition and uniform combustion to generate the maximum amount of heat possible, which, with normal care, can be used without any protective covering.

Yet a further object of this invention is to provide an improvement over the catalytic heater of applicant's allowed pending application Ser. No. 716,260, filed Aug. 20, 1976, now U.S. Pat. No. 4,068,651 granted Jan. 17, 1978.

BRIEF DESCRIPTION OF THE FIGURES

With the forgoing and other objects in view, this invention consists in the details of construction and combination of parts, as will be more fully understood from the following description, when read in conjunction with the accompanying drawings, in which.

DETAILED DESCRIPTION OF THE INVENTION

Figure 1:
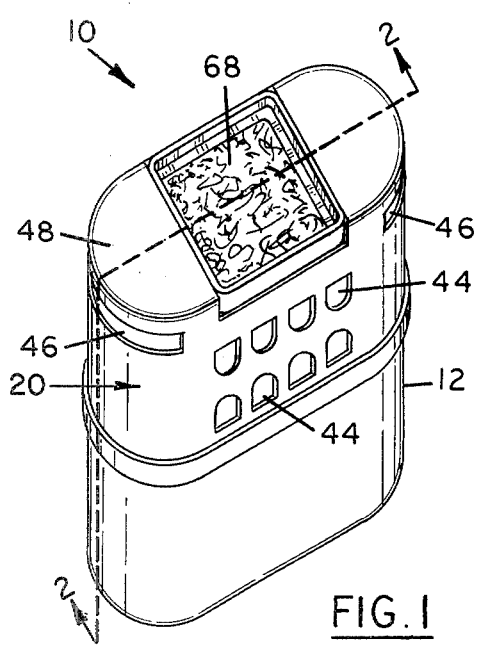
FIG. 1 is a perspective view of one form of the catalytic heater of this invention.

There is shown at 10 one form of the complete, assembled catalytic heater of this invention. The heater 10 includes a fuel cartridge 12 which is initially provided with readily openable hermetically sealed cover 14 having a pull handle 16 for manually removing the cover 14. A snap-on cover 18 is provided for then sealing the opened cartridge by snapping on the cover over cartridge edge 28 for use when only part of the fuel has been used up. Alternately, the snap-on cover 18 may be used initially when packaged, omitting the hermetically sealed cover 14 entirely.

After the cover is removed, the cartridge 12 is mated with the upper chimney section 20 for operation. Both the lower fuel containing cartridge 12 and the upper chimney section 20 are coated with a conventional heat insulating material 22 so as to retain the heat in cartridge 12 and chimney 20 and make the heater comfortable to use. An outwardly displaced mating flange 24 is provided on one of the sections, preferably the upper chimney section 20, for the lower fuel cartridge 12 is disposed of when its fuel contents are used up.

Figure 2:
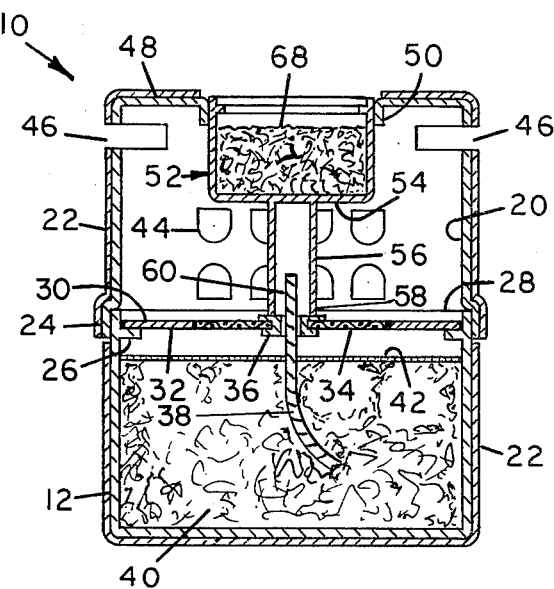
FIG. 2 is a vertical sectional view on line 2—2 of FIG. 1.
Figure 5:
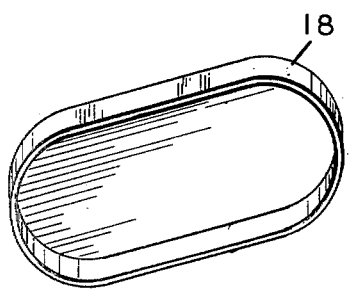
FIG. 5 is a perspective view of a snap-on lid for the fuel cartridge of FIGS. 4, 11 and 12.
Figure 3:
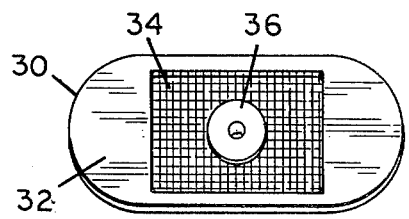
FIG. 3 is a perspective view of the catalytic member of FIG. 2.
Figure 4:
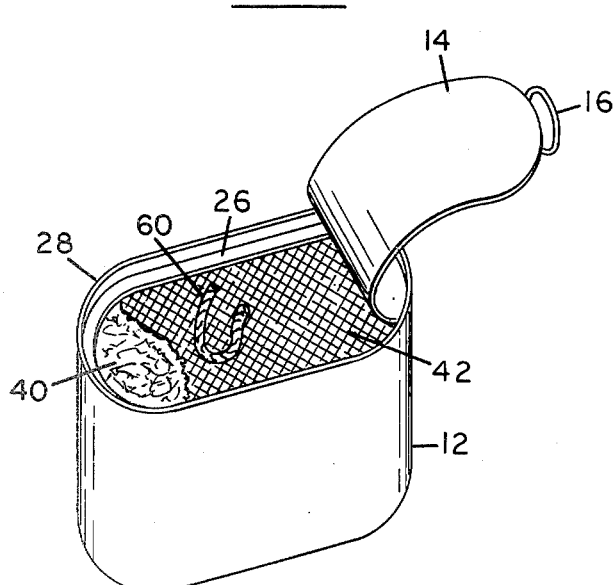
FIG. 4 is a perspective view of the fuel cartridge of FIG. 1 with the hermatically sealed lid partly removed.
Figure 7:
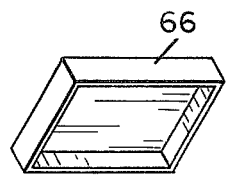
FIG. 7 is a perspective view of a snap-on lid for the container of FIG. 6.
Figure 6:
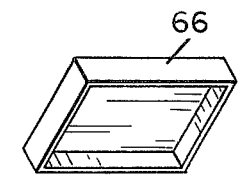
FIG. 6 is a perspective view of an insertable chemical container and snuffer tube combination, as in FIGS. 1 and 2.
Figure 8:
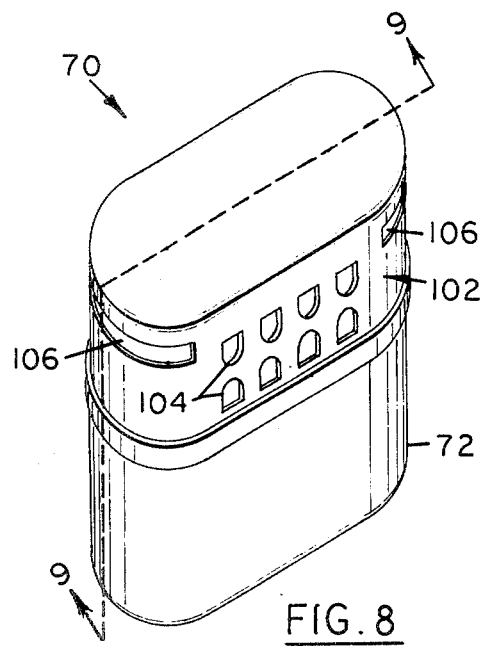
FIG. 8 is a perspective view of another form of catalytic heater of this invention.
Figure 9:
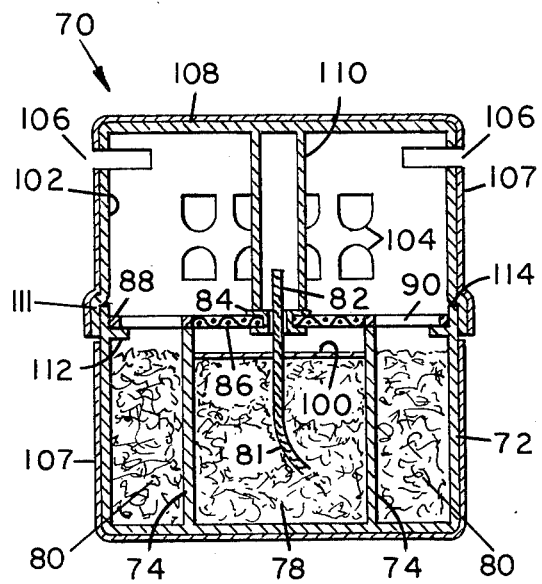
FIG. 9 is a verticle sectional view on line 9—9 of FIG. 8.
Figure 11:
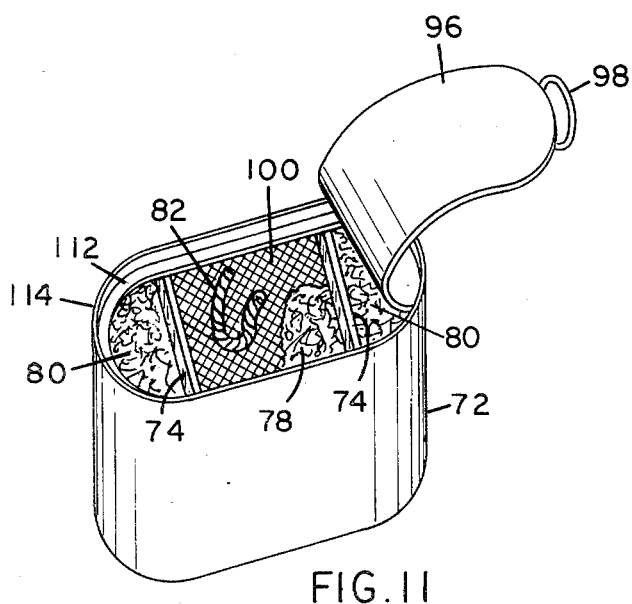
FIG. 11 is a perspective view of the partitioned cartridge of FIGS. 8, 9 and 12, with the hermetically sealed lid partly removed.
Figure 10:
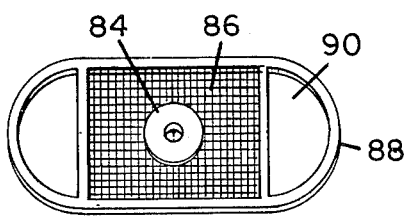
FIG. 10 is a perspective view of the catalytic member of FIG. 9.

A ledge 26 is located slightly below the top edge 28, and is always provided, whether or not the sealed cover 14 is provided, because it acts as a seat to receive and support the catalytic member 30 thereon, which is shown in FIG. 2.

This catalytic member 30 is made of a single plane plate 32 having a rectangular center portion occupied by catalytically impregnated stainless steel section, here shown as being of apporximately 0.00037 gauge, and may be either a foraminated stainless steel plate of this same gauge, or a stainless steel wire mesh screen 34 woven of approximately eighty strands to the inch. A central wick receiving opening therethrough is provided and this opening may have an eyelet 36 fixed thereabout in the screen 34 through which is extended a wick 38 extending upwardly from a fuel material 40 filling the cartridge 12, in which the liquid fuel has previously been absorbed to the desired amount. A fuel filter 42 of activated charcoal may be provided over the fuel containing absorbent material 40. The eyelet 36 may or may not be used in a foraminated plate catalytic member. Only a centrally located aperture of appropriate size to receive the wick 60 or 82 therethrough is needed.

The chimney section 20 is provided with two lower rows of air-admitting punched-in openings 44 in its opposite sides, and two oppositely disposed chimney combustion products exit openings 46 in its opposite oval ends adjacent the roof 48 thereon. The center of the roof 48 of the chimney section 20 is provided with an opening having an inturned edge 50 thereabout through which is inserted the chemical container 52.

Extending from the bottom 54 of chemical container 52 is a central flame snuffer tube 56 of such size that when the container 54 is inserted through the chimney top opening between ledges 50, the snuffer tube bottom edge 58 will just contact the mesh 34 or the eyelet, or the foranimous plate about the central opening and the snuffer tube 56 will surround the flaming wick top end 60 and extinguish the flame. The catalytic heating by the fuel through the catalytic member 34 may continue as long as fuel is present.

To stop the heating section, the chimney section 22 is removed from the fuel cartridge 12, and the snap-on cover 18 is put in place. Alternately, if the snap-on cover 18 is not available, the heating action may be discontinued by turning the heater 10 upside down and separating the fuel cartridge 12 from the chimney section 20 which will then remove contact of the catalyst from the fuel vapors. The chemical in container 52 is saturated, to the desired amount, in an absorbent material 68.

A sealed cover 62 on chemical container 52 has a pull handle 64 for manually removing it, and a snap-on cover 66 is provided for resealing it, if desired. Alternately, the snap-on cover 66 may be used initially when packaged, omitting the hermetically sealed cover 62 entirely.

There is shown at 70 another form of this invention. In form 70, a fuel and chemical containing cartridge 72 is provided with vertical partitions 74 providing a plurality of compartments 76, three compartments here being shown. In the center compartment a solid fuel, or a fuel absorbent material 78 is saturated with the desired amount of fuel, and in the side compartments, chemical absorbent materials 80 are saturated with the desired amount of chemical materials. The same or different materials may be provided in the separate chemical compartments.

The fuel or fuel absorbent material 78 in center compartment 76 has a wick 81 therein, whose top end 82 is extended up through a central opening in the mesh, or in the eyelet 84 in catalytic mesh 86, as in the first form. This mesh 86 is supported in a single plane frame 88, preferably of stainless steel. The frame 88 is oval in shape to fit in the top of oval cartridge 72, but is open at its ends 90, so that vapors from the chemical absorbent materials 80 may readily evaporate therethrough when the heater is in operation.

Figure 12:
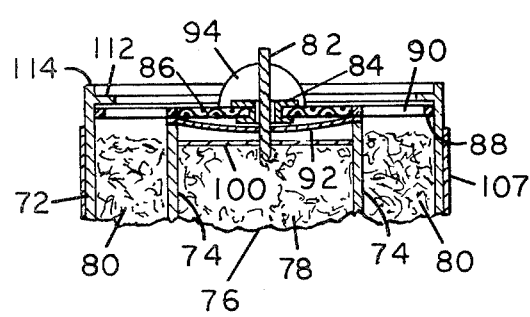
FIG. 12 is a fragmentary sectional view of the partitioned cartridge, but having the catalytic member installed within the hermetically sealed cartridge, and having a removable wrapper protecting the catalytic member from being contaminated by the liquid fuel while still sealed.

As shown in FIG. 12, the catalytic frame 88 may be prepackaged in the cartridge 72, in which case a moisture resistant wrapper 92 is packed thereunder, and provided with a tab 94. After removing cover 96 by pulling its handle 98, tab 94 is pulled to remove the wrapper 92, so that the fuel and chemicals may be evapoated when the heater is in use. A fuel filter 100 is provided over the center compartment 76 for the fuel in the fuel material 78.

The chimney section 102 of this form 70 has an outwardly displaced mating flange 111, which mates on cartridge 72 in the same manner that 20 is mated with 12 in heater 10. Air inlet holes 104 and combustion products exit slits 106 are similarly provided.

The chemical provided in either form are for any appropriate pupose, such as insect repellants or exterminators, air fresheners, deodorizers, etc.

Chimney section 102 and cartridge 72 are similarly insulated at 107 to retain the heat and to make the heater comfortable to use. At the bottom of the roof 108 of chimney section 102, there is provided a snuffer tube 110 to fit about the central opening in the mesh or plate or against eyelet 84 and surround the flaming wick top 82 to snuff out the flame when the chimney section 102 is mated with cartridge 72. An inwardly extending ledge 112 below the cartridge top edge 114 is left when removing the cover 96 to receive and support the catalytic member 88 thereon, and the same snap-on cover 18 of the first form may be used to seal this cartridge 72 when desired.

The chimney sections and the cartridge section of either form may be interchanged with that of the other form, if desired. Miscible fuels and chemicals may be used in cartridge 12, if desired, and the chimney section 102 of the second form may thus be used therewith.

Also, instead of chemicals in container 52, food or beverages may be provided, and it would then be made of appropriate size.

OPERATION OF THE INVENTION

To operate either form, the sealing cover is first removed from the fuel cartridge and the catalytic member is positioned in the top of the cartridge, if not already there, in which case the wrapper is removed by pulling its tab. The wick, having been extended through its opening or eyelet, is lit up and left burning until the catalytic action has been initiated, whereupon the chimney section is mated with the cartridge fuel section, thus snuffing out the flame and permitting the catalytic action to continue as long as desired, or until the fuel is exhausted. The catalytic action may be stopped, when desired, by removing the chimney section and either putting on the snap-on cover 18, or by turning it over, to remove contact of the catalyst with the fuel vapours. If the snap-on cover is used, it will keep the remaining fuel or chemical for future use; otherwise it may be lost by evaporation.

The heater 10 may be made in any desired size, from a pocket or hand warmer size to a camp or home food heater, to receive and heat commercially prepared containers of food of the desired size, or to receive any container of the proper size.

The term "foraminated", as used in this specification and its claims, means any article with some holes therethrough, whether it be a screen or any suitable material or a plate with holes formed therethrough. Thus, a metal plate with holes therethrough or a metal or plastic screen are both "foraminated" within the scope of this disclosure and its claims.

ABSTRACT OF THE DRAWINGS

In the drawings, like numbers refer to like parts and, for the purpose of explication, set forth below are the numbered parts of the DISPOSABLE CATALYTIC HEATER of this invention.
10 one form of this invention
12 fuel cartridge
14 hermetically sealed cover on 12
16 pull handle on 14
18 snap-on cover for 12 or 72
20 chimney section
22 heat insulating coating
24 outwardly displaced mating flange on 20
26 inwardly extending ledge in 12
28 top edge of cartridge 12
30 single plane catalytic frame member
32 plate of 30
34 catalyst impregnated mesh screen of frame member 30
36 eyelet in center of 34
38 wick
40 fuel absorbent material
42 fuel filter over 40
44 air admitting holes in chimney 20
46 combustion products exits
48 roof of 20
50 turned in edge of opening in 48
52 chemical container
54 bottom of 52
56 flame snuffer tube secured on 54
58 bottom end of 56
60 flame wick end of 38
62 sealed cover on 52
64 pull handle on 62
66 snap-on cover for 52
68 chemically saturated absorbent material in 52
70 second form of this invention
72 fuel and chemical containing cartridge
74 vertical partitions
76 center compartment
78 fuel absorbent material in center compartment 76
80 chemical absorbent materials in side compartments
81 wick
82 frame end of wick 81
84 eyelet
86 catalyst impregnated mesh screen of frame member 88
88 single plane catalytic frame member
90 open ends of 88 for chemical vapor to rise through
92 moisture resistant wrapper under 86
94 pull tab on 92
96 cartridge cover on 72
98 cover pulling handle 96
100 fuel filter over 78
102 chimney section
104 air inlet holes in chimney 102
106 combustion products exit openings
107 insulating coating
108 roof of 102
111 outwardly displaced mating flange on 102
112 inwardly extending ledge in 72
114 top edge of cartridge 72

Although this invention has been described in detail, such description is intended as being illustrative rather than limiting, since the invention may be variously embodied.

Having thus set forth and disclosed the nature of this invention, what is claimed is:

1. A catalytic heater (10, 70) comprising a sealed lower section fuel cartridge (12, 72), an upper chimney section (20, 102), said sealed lower section having a manually removable sealing cover (14, 18, 96), said sections having complementary mating edges (24, 28, 111, 114) in the absence of said sealing cover, said lower cartridge section having an inwardly extending ledge (26, 112) spaced somewhat below its mating edge (28, 114), said cartridge section having fuel material (40, 78) therein, both said sections having a heat insulating coating (22, 107) directly thereon, a catalytic member comprising a single plane frame member (30, 88) fitting on and supported on said ledge, a catalyst impregnated stainless steel member (34, 86) in said plane supported in said catalytic frame member over said fuel material, said stainless steel member having a wick receiving openings (36, 84) centrally located therein, a wick (38, 81) in said fuel material extendable up through said wick opening, a snuffer tube (56, 110) mounted centrally inside said chimney section and contacting said catalytic member about said wick (60,82) extending therethrough, said chimney section having a plurality of inlet openings (44, 104) adjacent its bottom edge and a plurality of combustion product exit openings (46, 106) adjacent its roof (48, 108).

2. The heater of claim 1, said snuffer tube (110) depending integrally from the roof (108) of said chimney section.

3. The heater of claim 1, said chimney section (20) having a container receiving opening (50) in its roof (48), a sealed container (52) extending snugly down through said roof opening and having said snuffer tube (56) extending integrally down from its bottom, said container having a readily removable cover (62, 66) thereon.

4. The heater of claim 1, said catalyst impregnated member being a mesh screen (34, 86) woven of stainless steel wire of approximately 0.0037 gauge and approximately eighty strands to the inch.

5. The heater of claim 1, said lower section having inwardly extending horizontal ledge means (112) providing support for said catalytic member, said lower cartridge having vertical partition means (74) dividing said lower section (72) into a plurality of compartments, one compartment (76) having fuel therein, and other compartments having liquid absorbent material (80) therein and liquid means therein that is non-miscible with said fuel.

6. The heater of claim 5, said vertical partition means including two vertical partitions (74) dividing said lower section into three compartments, the middle compartment (76) having liquid fuel absorbent material (78) and liquid fuel absorbed therein, said outer compartments having absorbent material (80) and liquids non-miscible with said fuel absorbed therein.

7. The heater of claim 6, said catalytic frame (88) having open ends (90) permitting vapors from said two outer compartments to rise therethrough when said heater is in operation.

8. The heater of claim 1, and a fuel vapor filter (42, 100) over said fuel.

9. The heater of claim 8, said filter being activated charcoal.

10. The heater of claim 1, said lower cartridge section (12, 72), prior to mating with said chimney section (20, 102), being a sealed container having a readily removable sealed cover member (14, 96), and a handle (16, 98) on said cover for manually pulling said cover off.

11. The heater of claim 1, said lower cartridge section, prior to mating with said chimney section, being a sealed container having a readily removable snap-on cover (18).

12. The heater of claim 1, said wick opening having an eyelet (36, 84) having an opening through which said wick (60, 82) extends.

13. The heater of claim 12, said snuffer tube contacting said eyelet when in snuffing position to hold said catalytic member in operative position.

14. The heater of claim 1, said catalytic member being located in said sealed lower cartridge below said cover ledge (112), and a moisture resistant wrapper (92) under said catalytic member.

15. The heater of claim 14, and an upwardly extending tab (94) for manually removing said wrapper for operation of said heater.

16. The heater of claim 1, said snuffer tube (56, 110) contacting said catalytic member (36, 84) about said wick receiving opening therethrough when in snuffing position to hold said catalytic member in operative position.

17. The heater of claim 1, said catalyst impregnated member being of foraminated stainless steel of approximately 0.0037 gauge.

18. The heater of claim 1, said catalyst impregnated member comprising a foraminated screen of approximately 0.0037 gauge.

19. The heater of claim 4, said catalyst member being impregnated with platinum.

20. The heater of claim 4, said catalyst member being impregnated with palladium.

* * * * *

UNITED STATES PATENT OFFICE
CERTIFICATE OF CORRECTION

Patent No. 4,174,702          Dated  Nov. 20, 1979

Inventor(s) ALFRED A. RAPPAPORT

It is certified that error appears in the above-identified patent and that said Letters Patent are hereby corrected as shown below:

Col. 3, line 45, "0.00037" should be  --0.0037--.

Col. 6, line 25, "frame" should be --flame--.

Col. 6, between lines 40 and 41, insert

--110 snuffer tube in 102 secured integrally to roof 108--.

Signed and Sealed this

Twenty-sixth Day of February 1980

[SEAL]

Attest:

SIDNEY A. DIAMOND

Attesting Officer        Commissioner of Patents and Trademarks